United States Patent
Antony et al.

(10) Patent No.: US 11,051,689 B2
(45) Date of Patent: Jul. 6, 2021

(54) REAL-TIME PASSIVE MONITORING AND ASSESSMENT OF PEDIATRIC EYE HEALTH

(71) Applicant: INTERNATIONAL BUSINESS MACHINES CORPORATION, Armonk, NY (US)

(72) Inventors: Bhavna Josephine Antony, Brunswick East (AU); Suman Sedai, Hughesdale (AU); Dwarikanath Mahapatra, Melbourne (AU); Rahil Garnavi, Macleod (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 143 days.

(21) Appl. No.: 16/178,757

(22) Filed: Nov. 2, 2018

(65) Prior Publication Data
US 2020/0138285 A1    May 7, 2020

(51) Int. Cl.
*A61B 3/11*   (2006.01)
*A61B 3/10*   (2006.01)
(Continued)

(52) U.S. Cl.
CPC .............. *A61B 3/101* (2013.01); *A61B 3/112* (2013.01); *A61B 3/113* (2013.01); *A61B 3/14* (2013.01);
(Continued)

(58) Field of Classification Search
CPC ........... A61B 3/113; A61B 3/102; A61B 3/13; A61B 5/163; A61B 2503/06
(Continued)

(56) References Cited

U.S. PATENT DOCUMENTS 7,963,655 B2   6/2011  Huth et al.
8,909,327 B1   12/2014  Bosworth
(Continued)

FOREIGN PATENT DOCUMENTS

CN    106921806 A    7/2017
EP      1900320 A1   3/2008
(Continued)

OTHER PUBLICATIONS

Busin et al. "Automated corneal topography: Computerized analysis of photokeratoscope images", Graefe's Archive for Clinical and Experimental Ophthalmology, May 1989, vol. 227, Issue 3, pp. 230-236.
(Continued)

*Primary Examiner* — Hung X Dang
(74) *Attorney, Agent, or Firm* — Kenneth Han

(57) ABSTRACT

A method, computer system, and computer program product for real-time pediatric eye health monitoring and assessment are provided. The embodiment may include receiving a plurality of real-time data related to an individual's eye health from a user device. The embodiment may also include assessing biometric indications relating to eye health based on the plurality of real-time data. The embodiment may further include generating a report on the assessed biometric indications. The embodiment may also include collecting clinical information from one or more databases. The embodiment may further include determining whether the assessed biometric indications reach pre-configured threshold conditions. The embodiment may also include generating alerts and recommendations based on analysis of the collected clinical information and the assessed biometric indications based on the assessed biometric indications satisfying the pre-configured threshold conditions.

20 Claims, 7 Drawing Sheets

(51) Int. Cl.
*A61B 3/14* (2006.01)
*G02B 27/00* (2006.01)
*A61B 3/113* (2006.01)
*A61B 5/00* (2006.01)
*G06K 9/22* (2006.01)
*G06K 9/00* (2006.01)

(52) U.S. Cl.
CPC ........ *A61B 5/6898* (2013.01); *G02B 27/0093* (2013.01); *G06K 9/00912* (2013.01); *G06K 9/22* (2013.01)

(58) Field of Classification Search
USPC .......................... 351/209, 210, 205, 200, 246
See application file for complete search history.

(56) References Cited

U.S. PATENT DOCUMENTS

| | | | |
|---|---|---|---|
| 9,314,154 | B2 | 4/2016 | Palanker et al. |
| 9,433,346 | B2 | 9/2016 | Huang |
| 2007/0126985 | A1 | 6/2007 | Wiltberger et al. |
| 2011/0176106 | A1 | 7/2011 | Lewkowski |
| 2013/0155376 | A1 | 6/2013 | Huang et al. |
| 2013/0235346 | A1* | 9/2013 | Huang .................. A61B 3/152 351/208 |
| 2014/0340642 | A1 | 11/2014 | You et al. |
| 2015/0342457 | A1 | 12/2015 | Sanchez Ramos et al. |
| 2016/0073869 | A1 | 3/2016 | Bailey |
| 2017/0000683 | A1 | 1/2017 | Samec et al. |
| 2017/0007450 | A1 | 1/2017 | Samec et al. |
| 2017/0131291 | A1 | 5/2017 | Huang |
| 2017/0258319 | A1 | 9/2017 | Weffers-Albu et al. |
| 2018/0256023 | A1 | 9/2018 | Swital et al. |
| 2019/0290118 | A1 | 9/2019 | Jha et al. |

FOREIGN PATENT DOCUMENTS

| | | |
|---|---|---|
| EP | 3199096 A2 | 8/2017 |
| GB | 2524500 A | 9/2015 |
| IN | 201811022652 A | 7/2018 |
| WO | 2007128851 A1 | 11/2007 |
| WO | 2014210571 A1 | 12/2014 |
| WO | 2016198902 A1 | 12/2016 |
| WO | 2016203212 A2 | 12/2016 |
| WO | 2017143091 A1 | 8/2017 |

OTHER PUBLICATIONS

Cooper et al., "What is Amblyopia or Lazy Eye?", Treatment of Amblyopia, Lazy Eye or Strabismus, http://www.strabismus.org/amblyopia_lazy_eye.html, accessed Sep. 25, 2018, 4 pages.

Divjak et al., "Eye blink based fatigue detection for prevention of Computer Vision Syndrome", MVA2009 IAPR Conference on Machine Vision Applications, May 20-22, 2009, Yokohama, Japan, pp. 350-353.

Kozeis, "Impact of computer use on children's vision", Hippokratia Quarterly Medical Journal, https://www.ncbi.nlm.nih.gov/pmc/articles/PMC2776336/, Oct.-Dec. 2009, vol. 13, Issue 4, pp. 230-231.

Mahapatra et al., "Image Super Resolution Using Generative Adversarial Networks and Local Saliency Maps for Retinal Image Analysis", 20th International Conference of Medical Image Computing and Computer-Assisted Intervention (MICCAI 2017), Part III, Part of the Lecture Notes in Computer Science (LNCS) book series vol. 10435, Quebec City, QC, Canada, Sep. 11-13, 2017, pp. 382-390.

Mell et al., "The NIST Definition of Cloud Computing", Recommendations of the National Institute of Standards and Technology, Special Publication 800-145, Sep. 2011, 7 pages.

Rashidi et al., "Computer vision syndrome prevalence, knowledge and associated factors among Saudi Arabia University Students: Is it a serious problem?", International Journal of Health Sciences, vol. 11, Issue 5, Nov.-Dec. 2017, pp. 17-19.

\* cited by examiner

REAL-TIME PASSIVE MONITORING AND ASSESSMENT OF PEDIATRIC EYE HEALTH

BACKGROUND

The present invention relates, generally, to the field of computing, and more particularly to pediatric eye health assessment.

It goes without saying that pediatric eye health assessments are crucial as acute conditions that are not addressed in an early stage of childhood may lead to chronic conditions. Excessive usage of mobile devices, such as smartphones and tablets, may result in computer vision syndrome. Computer vision syndrome may include dry eyes, eye strain, double vision, and headaches. Also, excessive rubbing of eyes due to discomfort caused by fatigue or eye dryness may lead to keratoconus, a chronic condition that affects vision due to changes in the shape and structural integrity of a cornea. Addressing computer vision syndrome and the symptoms associated with it will be more important as the use and availability of digital devices is on the rise. The early and rapid detection of developing myopia is also a concern, as young patients may not be able to communicate these problems, which include blurry vision and headaches, adequately.

SUMMARY

According to one embodiment, a method, computer system, and computer program product for real-time pediatric eye health monitoring and assessment are provided. The embodiment may include receiving a plurality of real-time data related to an individual's eye health from a user device. The embodiment may also include assessing biometric indications relating to eye health based on the plurality of real-time data. The embodiment may further include generating a report on the assessed biometric indications. The embodiment may also include collecting clinical information from one or more databases. The embodiment may further include determining whether the assessed biometric indications reach pre-configured threshold conditions. The embodiment may also include generating alerts and recommendations based on analysis of the collected clinical information and the assessed biometric indications based on the assessed biometric indications satisfying the pre-configured threshold conditions.

BRIEF DESCRIPTION OF THE SEVERAL VIEWS OF THE DRAWINGS

These and other objects, features, and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
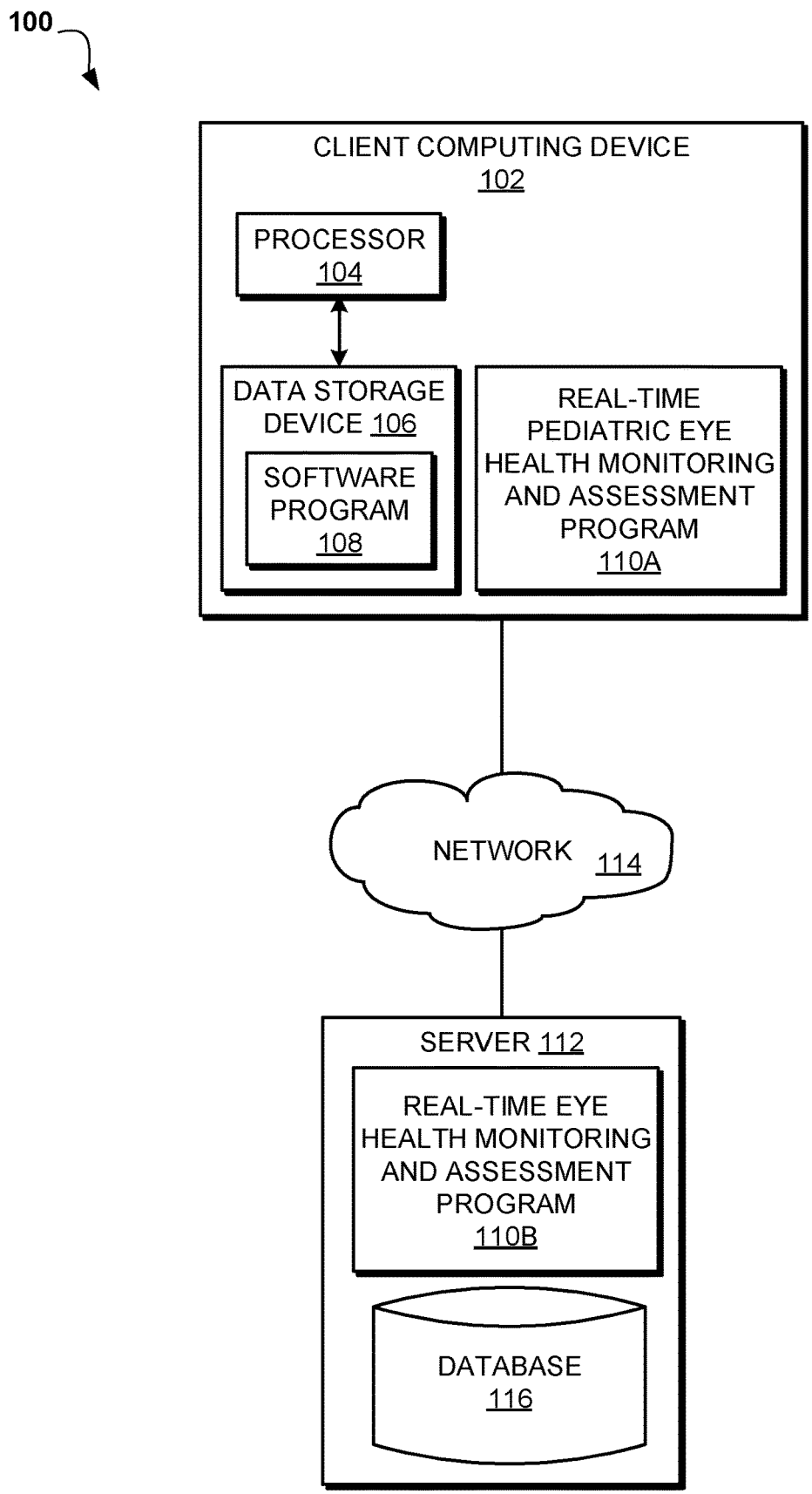
FIG. 1 illustrates an exemplary networked computer environment according to at least one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate to the field of computing, and more particularly to real-time pediatric eye health monitoring and assessment systems. The following described exemplary embodiments provide a system, method, and program product to, among other things, allow a user to continuously and passively monitor a child's eyes in a real-time and non-clinical setting using mobile devices. Therefore, the present embodiment has the capacity to improve the technical field of pediatric eye health monitoring systems by allowing users to easily assess a child's eye health on a daily basis without utilizing complex medical devices.

As previously described, pediatric eye health assessment may relate to monitoring and assessing pediatric eye conditions in an early stage of childhood to prevent them from becoming chronic conditions in the future. Computer vision syndrome caused by excessive usage of mobile devices may include dry eye, eye strain, double vision and headaches. Also, excessive rubbing of eyes due to discomfort caused by fatigue or eye dryness may lead to keratoconus, a chronic condition that affects vision due to changes in the shape and structural integrity of a cornea. Addressing computer vision syndrome and the symptoms associated with it will be more important as the use and availability of digital devices is on the rise. The early and rapid detection of developing myopia is also a concern, as young patients may not be able to communicate these problems, which include blurry vision and headaches, adequately.

Pediatric eye examinations are inherently difficult to conduct as young patients are often non-compliant. In addition, typical monitoring devices related to eye health in general mostly utilize headsets or other medical devices. For example, specific systems proposed for the detection of dry eye may include the use of interferometry or require the analysis of tear samples. Previously proposed eye-health monitoring systems have targeted the analysis of visual function in adults specifically with regard to age-related muscular degermation or glaucoma. As all these monitoring systems require patient feedback, it may be difficult to obtain feedback from young patients. As such, it may be advantageous to, among other things, implement a system capable of monitoring and assessing a child's eye health in a real-time setting utilizing mobile devices and generate and provide analysis reports to the child's parents and ophthalmologists so that they can take preventive measures in time.

According to one embodiment, a real-time pediatric eye health monitoring and assessment program may utilize a user's mobile devices, such as smartphones, tablets or laptops to monitor the distance of a user's eyes from a device screen, blink rate of a user, gestures, tear film integiry and the distance between a user's pupils. In at least one embodiment, a real-time pediatric eye health monitoring and assessment program may store the monitored data in databases and may generate alerts and recommendations based on clinical knowledge obtained from the databases.

The present invention may be a system, a method, and/or a computer program product at any possible technical detail level of integration. The computer program product may include the computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer-readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or another device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product for monitoring and assessing a child's eye health in a real-time setting utilizing mobile devices and generating analysis reports.

Referring to FIG. 1, an exemplary networked computer environment 100 is depicted, according to at least one embodiment. The networked computer environment 100 may include client computing device 102 and a server 112 interconnected via a communication network 114. According to at least one implementation, the networked computer environment 100 may include a plurality of client computing devices 102 and servers 112 of which only one of each is shown for illustrative brevity.

The communication network 114 may include various types of communication networks, such as a wide area network (WAN), local area network (LAN), a telecommunication network, a wireless network, a public switched network and/or a satellite network. The communication network 114 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements.

Client computing device 102 may include a processor 104 and a data storage device 106 that is enabled to host and run a software program 108 and a real-time pediatric eye health monitoring and assessment program 110A and communicate with the server 112 via the communication network 114, in accordance with one embodiment of the invention. Client computing device 102 may be, for example, a mobile device, a telephone, a personal digital assistant, a netbook, a laptop computer, a tablet computer, a desktop computer, or any type of computing device capable of running a program and accessing a network. As will be discussed with reference to FIG. 5, the client computing device 102 may include internal components 502a and external components 504a, respectively.

The server computer 112 may be a laptop computer, netbook computer, personal computer (PC), a desktop computer, or any programmable electronic device or any network of programmable electronic devices capable of hosting and running a real-time eye health monitoring and assessment program 110B and a database 116 and communicating with the client computing device 102 via the communication network 114, in accordance with embodiments of the invention. As will be discussed with reference to FIG. 5, the server computer 112 may include internal components 502b and external components 504b, respectively. The server 112 may also operate in a cloud computing service model, such as Software as a Service (SaaS), Platform as a Service (PaaS), or Infrastructure as a Service (IaaS). The server 112 may also be located in a cloud computing deployment model, such as a private cloud, community cloud, public cloud, or hybrid cloud.

According to the present embodiment, the real-time pediatric eye health monitoring and assessment program 110A, 110B may be a program capable of monitoring multiple biomarkers, such as blink rate, distance from the screen, gestures of rubbing eyes and tear film break-up to report on common pediatric eye health problems. The real-time pediatric eye health monitoring and assessment program 110A, 110B may also track, monitor and generate trend reports with respect to the monitored biomarkers. The real-time pediatric eye health monitoring and assessment process is explained in further detail below with respect to FIG. 2.

Figure 2:
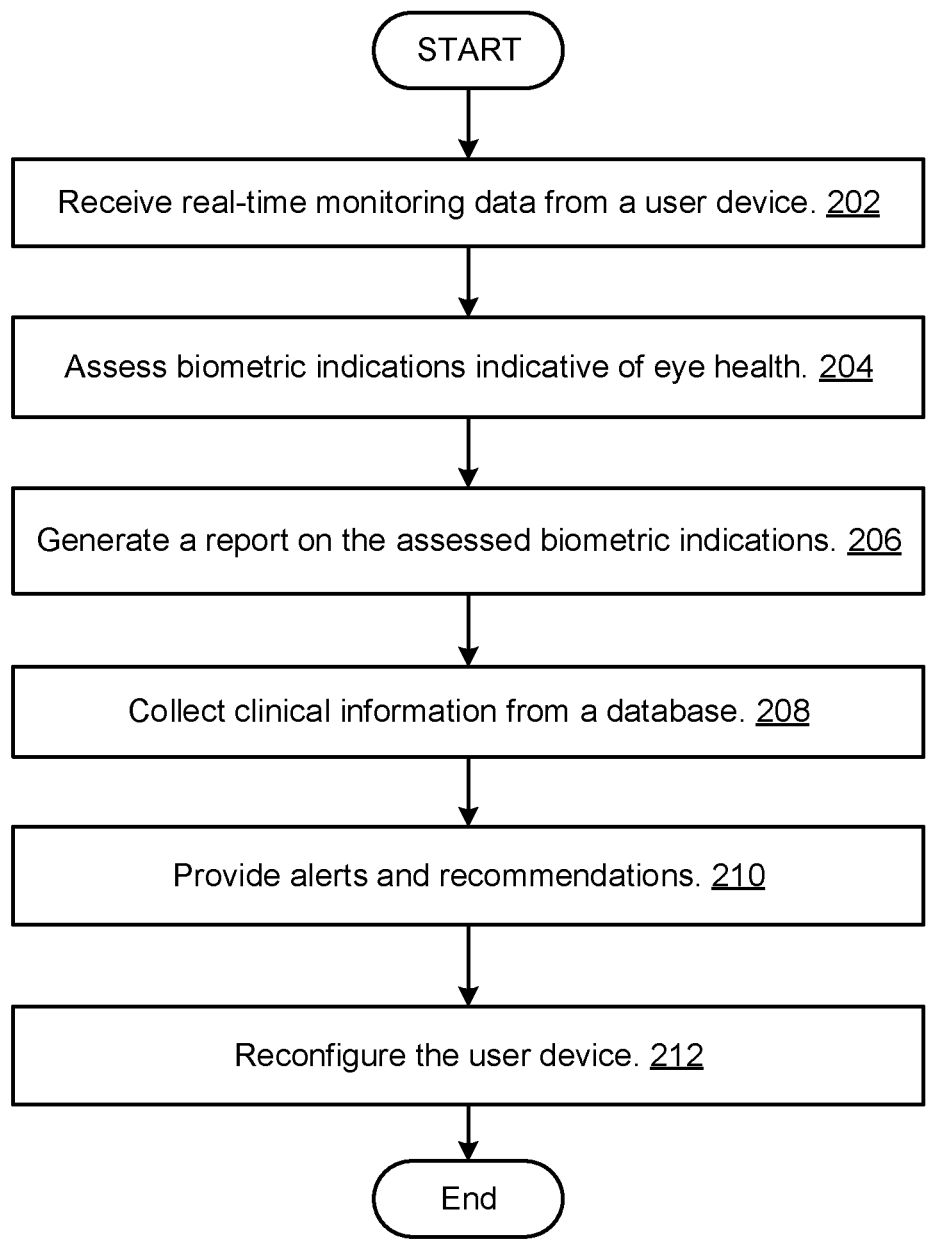
FIG. 2 is an operational flowchart illustrating a real-time pediatric eye health monitoring and assessment process according to at least one embodiment.

FIG. 2 is an operational flowchart illustrating a real-time pediatric eye health monitoring and assessment process 200 according to at least one embodiment. At 202, the real-time pediatric eye health monitoring and assessment program 110A, 110B receives real-time data from a user device. According to one embodiment, the real-time pediatric eye health monitoring and assessment program 110A, 110B may capture information related to a user's eye health from a device including a camera, an eye-tracking software and an infra-red sensor. The real-time pediatric eye health monitoring and assessment program 110A, 110B may also receive information related to external environmental factors affecting eye health, such as temperature, humidity, lighting conditions, and air flow from a home monitoring system. In at least one embodiment, the real-time pediatric eye health monitoring and assessment program 110A, 110B may receive information as to the distance of a user's eyes from a device screen, a blink rate of a user, gestures (e.g., rubbing eyes), tear film integrity and distance between two pupils. In at least one other embodiment, the real-time pediatric eye health monitoring and assessment program 110A, 110B may receive information manually entered by a user. For example, a user may manually enter a child's pre-existing eye conditions, such as refractive error, select specific temperature, lighting condition or humidity inside a house when the child is watching a video on a smartphone.

At 204, the real-time pediatric eye health monitoring and assessment program 110A, 110B assesses biometric indications relevant of eye health. According to one embodiment, the real-time pediatric eye health monitoring and assessment program 110A, 110B may assess a child's eye health by analyzing the data obtained in step 202. For example, the real-time pediatric eye health monitoring and assessment program 110A, 110B may compute the distance between a child's eye and a device screen and determine if it is within a safe range given the child's age. The real-time pediatric eye health monitoring and assessment program 110A, 110B may also calculate a child's blink rate based on a number of blinks per minute captured by a camera or video system mounted on a user device. The real-time pediatric eye health monitoring and assessment program 110A, 110B may also interpret a child's gestures captured by a camera or video system. For example, the real-time pediatric eye health monitoring and assessment program 110A, 110B may determine that a child has a dry eye when the child excessively rubs his eyes or the blink rate increases. The real-time pediatric eye health monitoring and assessment program 110A, 110B may further calculate a distance between two pupils of a child while watching a video or playing a game on a smartphone based on the captured information in step 202.

In addition, the real-time pediatric eye health monitoring and assessment program 110A, 110B may assess a child's tear film integrity. Human tear film is an oil or lipid-based layer which helps reduce evaporation of natural tears and prevent eye dryness. According to one embodiment, the real-time pediatric eye health monitoring and assessment program 110A, 110B may track and detect a child's pupils utilizing a camera. The real-time pediatric eye health monitoring and assessment program 110A, 110B then may localize a tear film reflection by determining which region of certain display (e.g. game, video or pictures) is reflected on the tear film. The real-time pediatric eye health monitoring and assessment program 110A, 110B may also simulate what the reflection may look like in the tear film utilizing a deep-learning generative model which may be compared to the detected reflection of the display on the child's tear film. The real-time pediatric eye health monitoring and assessment program 110A, 110B may further utilize an infra-red sensor to localize the pupils and the amplitude of the reflected light from the child's eyes. In at least one embodiment, the real-time pediatric eye health monitoring and assessment program 110A, 110 may obtain three metrics with respect to the tear film integrity: (1) the time taken for tear film breakup; (2) the quadrant of the pupil where the breakup begins; and (3) the ratio of the area of the broken tear film to the total pupil.

At 206, the real-time pediatric eye health monitoring and assessment program 110A, 110B generates a report on the assessed biometric indications. According to one embodiment, the real-time pediatric eye health monitoring and assessment program 110A, 110 B may generate both a short-term and a long-term report summarizing the assessed biometric indications. For example, the real-time pediatric eye health monitoring and assessment program 110A, 110B may generate graphs and charts to show how the data associated with the distance of a child's eyes from a device screen, blink rate, gestures, tear film integrity and distance between pupils change over a certain period of time. The graphs and charts may be used as a daily trend report, which shows frequency and duration of each usage of a mobile device by a child and represents how each assessed data change in each instance of the device usage. In at least one other embodiment, the real-time pediatric eye health monitoring and assessment program 110A, 110B may store the generated reports in a cloud based long-term storage database allowing a user to retrieve the reports when they are needed.

At 208, the real-time pediatric eye health monitoring and assessment program 110A, 110B collects clinical information from a database. According to one embodiment, the real-time pediatric eye health monitoring and assessment program 110A, 110B may receive clinical information related to relationships between certain eye disease symptoms and the observed blink rate, gestures and tear film integrity. For example, the real-time pediatric eye health monitoring and assessment program 110A, 110B may receive clinical information regarding trends in excessive eye rubbing and the development of chronic dry eye. A user also may receive clinical data as to an average blink rate or average distance between pupils for a child in a certain age group so that the user may compare the assessed blink rate or the measured distance to the clinical data.

At 210, the real-time pediatric eye health monitoring and assessment program 110A, 110B provides alerts and recommendations. According to one embodiment, the real-time pediatric eye health monitoring and assessment program 110A, 110B may send alerts to a user when monitored biometric indications reaches certain threshold predetermined by the real-time pediatric eye health monitoring and assessment program 110A, 110B based on the collected clinical information. For example, the real-time pediatric eye health monitoring and assessment program 110A, 110B may send an alert to a user through a user device screen or as an SMS to a registered number when the excessive rubbing of the eyes of a child is monitored in a real-time setting. If the alert is critical, the real-time pediatric eye health monitoring and assessment program 110A, 110B may automatically turn off the display screen which the child was watching.

The real-time pediatric eye health monitoring and assessment program 110A, 110B may also generate recommendations regarding continued usage of a mobile device by a child based on previously developed model according to one other embodiment. The real-time pediatric eye health monitoring and assessment program 110A, 110B may augment the recommendations with a display system or home automation system. For example, if the real-time pediatric eye health monitoring and assessment program 110A, 110B determines that a child's computer vision syndrome is deemed to be worsening, the real-time pediatric eye health monitoring and assessment program 110A, 110B may recommend a reduction in the total allowed screen time or a change in the surrounding conditions, such as humidity or lighting. In at least one other embodiment, the real-time pediatric eye health monitoring and assessment program 110A, 110B may learn specifics about each individual and store the information in a plurality of databases such that the real-time pediatric eye health monitoring and assessment program 110A, 110B may avoid providing population-wide general guidelines to each user. According to one other embodiment, the real-time pediatric eye health monitoring and assessment program 110A, 110B may automatically or manually send the alerts or recommendations to a child's pediatric ophthalmologist to schedule an appointment.

At 212, the real-time pediatric eye health monitoring and assessment program 110A, 110B reconfigures the user device. According to one embodiment, the real-time pediatric eye health monitoring and assessment program 110A, 110B may reconfigure the brightness, size and resolution of a device screen based on the generated alerts and recommendations. For example, if the real-time pediatric eye health monitoring and assessment program 110A, 110B determines that a child is viewing a display screen of a smartphone or a personal computer too closely, then it may reconfigure the display system to make graphics brighter or larger, display an alerting message or turn off the screen itself.

Figure 3:
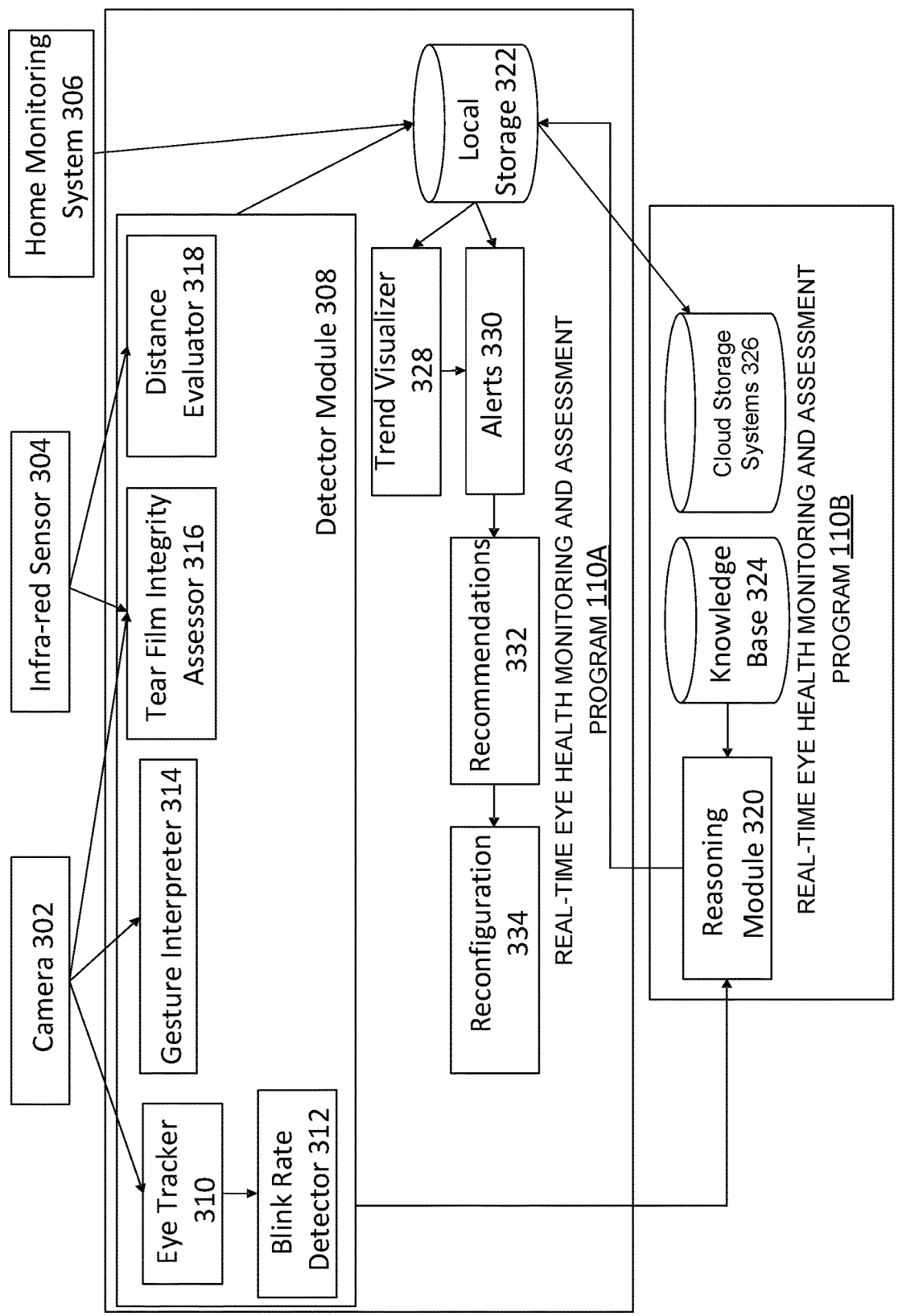
FIG. 3 is a functional block diagram of a real-time pediatric eye health monitoring and assessment platform according to at least one embodiment.

Referring now to FIG. 3, a functional block diagram of a real-time pediatric eye health monitoring and assessment process 300 is depicted according to at least one embodiment. According to one embodiment, the real-time pediatric eye health monitoring and assessment program 110B may capture information related to a child's eye health from a camera 302, an infra-red sensor 304, and a home monitoring system 306. The real-time pediatric eye health monitoring and assessment program 110A may include a detector module 308, a reasoning module 320 and one or more local storage 322. The detector module 308 may include an eye tracker 310, a blink rate detector 312, a gesture interpreter 314, a tear film integrity assessor 316 and a distance evaluator 318. The eye tracker 310 may assess a distance of a child's eyes from a device screen. The blink detector 312 may measure a blink rate of a child while the child is viewing a device screen. The gesture interpreter 314 may capture and assess particular behaviors of a child, such as squinting or eye rubbing. The tear film integrity assessor 316 may assess how fast a tear film breaks up or the ratio of the area of the broken tear film to the total pupil. The distance evaluator 318 may track positions of pupils and the distance between them. The reasoning module 320 may then analyze the assessed information and send alerts 330 to a user. For example, the reasoning module 320 may send a message to a user to turn off the device or notify a user that the screen is too close to a child's face. The reasoning module 320 may send the analyzed data to one or more local storages 322 so that the real-time pediatric eye health monitoring and assessment program 110A may keep the records for future reference. The reasoning module 320 may also collect clinical information related to certain symptoms from one or more knowledge databases 324 to compare the assessed information to more general information. The local storage 322 may also store the information in one or more cloud storage systems 326. The local storage 322 may generate a trend visualization 328 including graphs and charts depicting the change or deviation of the assessed data over a certain period of time. The real-time pediatric eye health monitoring and assessment program 110A may also utilize the stored information in one or more local storage 322 to generate recommendations 332. The real-time pediatric eye health monitoring and assessment program 110A may then reconfigure a user device's display settings based on the alerts 330 and the recommendations 332.

Figure 4:
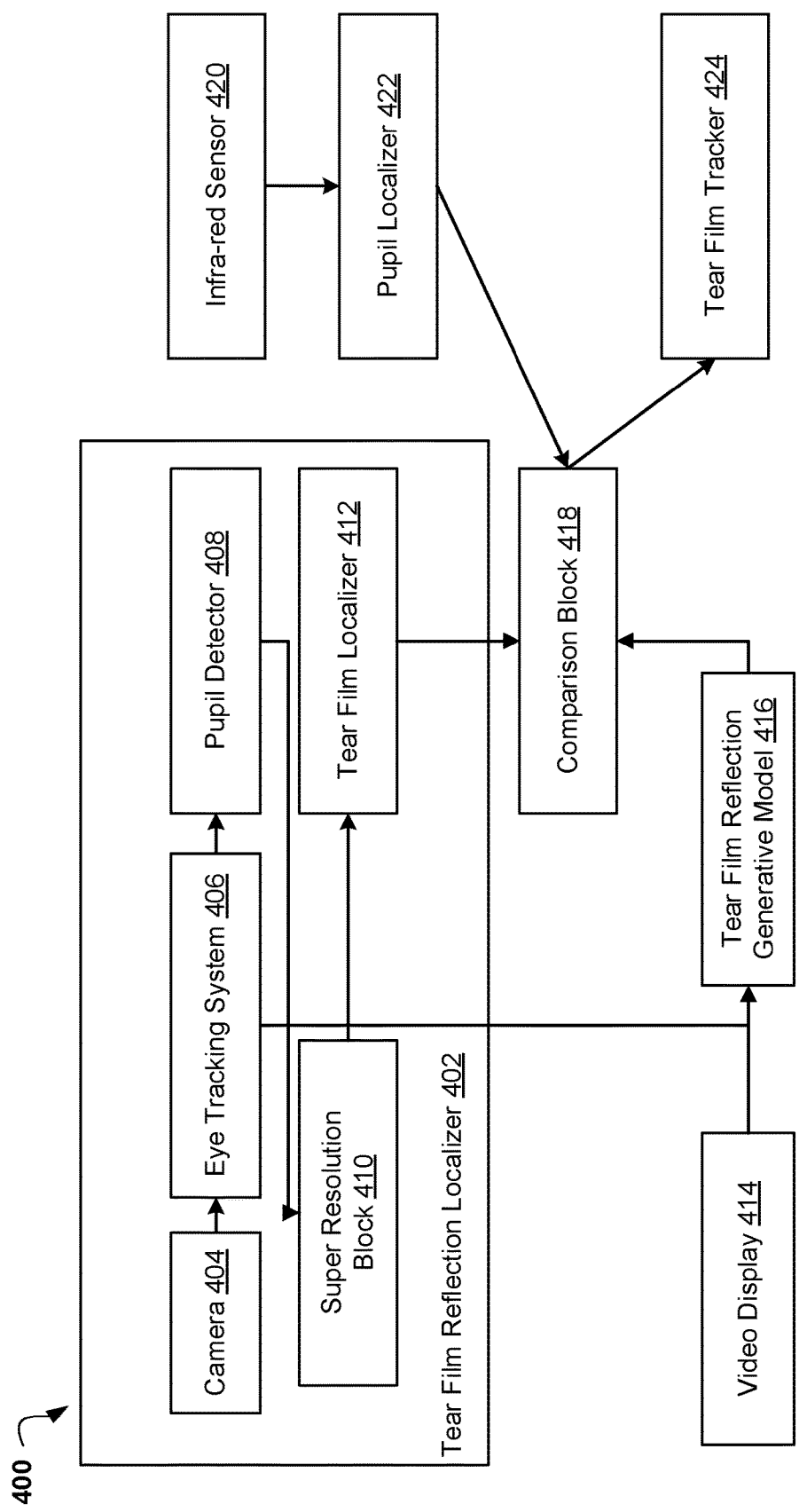
FIG. 4 is a functional block diagram of a tear film metrics generation platform according to at least one embodiment.

Referring now to FIG. 4, a functional block diagram of a tear film metrics generation platform 400 is depicted according to at least one embodiment. According to one embodiment, the real-time pediatric eye health monitoring and assessment program 110A, 110B may include a tear film reflection localizer 402 consisting of a camera 404, an eye tracking system 406, a pupil detector 408, a super resolution block 410, and a tear film localizer 412. The tear film reflection localizer 402 may receive images of eyes from an on-board camera utilizing the eye tracking system 406. The pupil detector 408 may detect the locations of pupils. As the images of the detected pupils are derived from the on-board camera, the super resolution block 410 may need to improve the resolution of the images. Once the resolution of the images is improved, the tear film localizer 412 may detect the tear film reflection and localize the tear film. A tear film reflection generative model 416 may utilize feedback from a video display 414 and the eye tracking system 406 to determine which region of the display (video, pictures, games, etc.) is reflected on the tear film. The tear film reflection generative model 416 may process the identified region of the display to simulate what the actual reflection will look like in the real tear film. In at least one other embodiment, the tear film reflection generative model may utilize deep-learning technologies. An infra-red sensor 420 and a pupil localizer 422 may localize pupils and detect the amplitude of the reflected light from the tear film. A comparison block 418 may consist of two sub-modules: (1) a tear film reflection analyzer; and (2) an infra-red reflection analyzer. The tear film reflection analyzer may compare the localized tear film and the pupils to the tear film reflection generative model 416. The infra-red reflection analyzer may monitor any deviations from a normative reflection model. Once the comparison block 418 completes the analyses, a tear film tracker 424 may provide three metrics concerning the tear film integrity: (1) the time taken for the tear film break-up; (2) the quadrant of the pupil where the break-up begins; and (3) the ratio of the area of the broken tear film to an entire pupil.

It may be appreciated that FIGS. 2-4 provide only an illustration of one implementation and do not imply any limitations with regard to how different embodiments may be implemented. Many modifications to the depicted environments may be made based on design and implementation requirements. For example, in at least one embodiment, the real-time pediatric eye health monitoring and assessment program 110A, 110B may utilize a machine-learning prediction module that analyzes longitudinal data and generates predictions.

Figure 5:
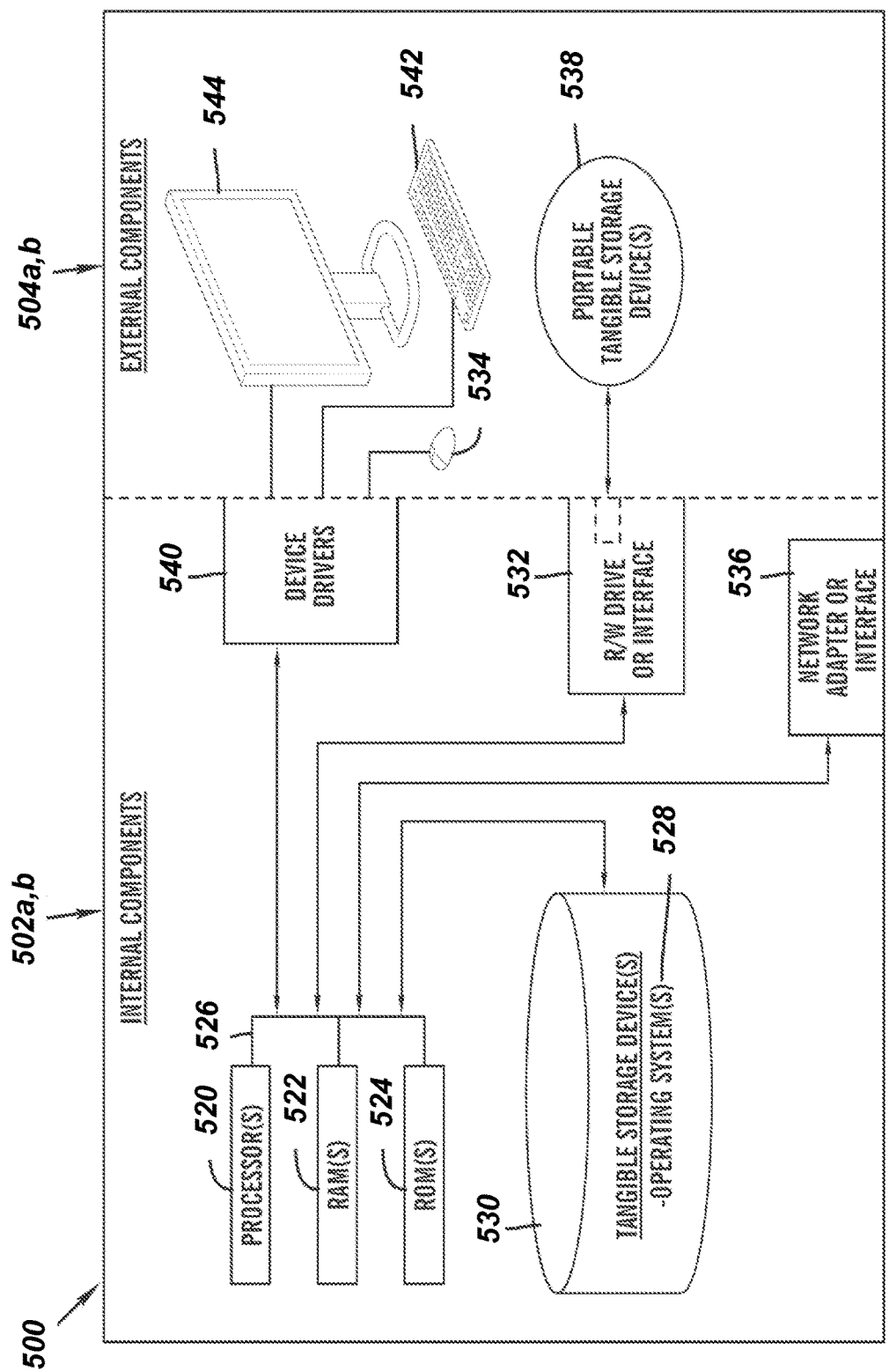
FIG. 5 is a block diagram of internal and external components of computers and servers depicted in FIG. 1 according to at least one embodiment.

FIG. 5 is a block diagram 500 of internal and external components of the client computing device 102 and the server 112 depicted in FIG. 1 in accordance with an embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

The data processing system 502, 504 is representative of any electronic device capable of executing machine-readable program instructions. The data processing system 502, 504 may be representative of a smart phone, a computer system, PDA, or other electronic devices. Examples of computing systems, environments, and/or configurations that may represented by the data processing system 502, 504 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The client computing device 102 and the server 112 may include respective sets of internal components 502 a,b and external components 504 a,b illustrated in FIG. 5. Each of the sets of internal components 502 include one or more processors 520, one or more computer-readable RAMs 522, and one or more computer-readable ROMs 524 on one or more buses 526, and one or more operating systems 528 and one or more computer-readable tangible storage devices 530. The one or more operating systems 528, the software program 108 and the real-time pediatric eye health monitoring and assessment program 110A in the client computing device 102 and the real-time pediatric eye health monitoring and assessment program 110B in the server 112 are stored on one or more of the respective computer-readable tangible storage devices 530 for execution by one or more of the respective processors 520 via one or more of the respective RAMs 422 (which typically include cache memory). In the embodiment illustrated in FIG. 5, each of the computer-readable tangible storage devices 530 is a magnetic disk storage device of an internal hard drive. Alternatively, each of the computer-readable tangible storage devices 530 is a semiconductor storage device such as ROM 424, EPROM, flash memory or any other computer-readable tangible storage device that can store a computer program and digital information.

Each set of internal components 502 a,b also includes an R/W drive or interface 532 to read from and write to one or more portable computer-readable tangible storage devices 538 such as a CD-ROM, DVD, memory stick, magnetic tape, magnetic disk, optical disk or semiconductor storage device. A software program, such as the real-time pediatric eye health monitoring and assessment program 110A, 110B, can be stored on one or more of the respective portable computer-readable tangible storage devices 538, read via the respective R/W drive or interface 532 and loaded into the respective hard drive 530.

Each set of internal components 502 a,b also includes network adapters or interfaces 536 such as a TCP/IP adapter cards, wireless Wi-Fi interface cards, or 3G or 4G wireless interface cards or other wired or wireless communication links. The software program 108 and the real-time pediatric eye health monitoring and assessment program 110A in the client computing device 102 and the real-time pediatric eye health monitoring and assessment program 110B in the server 112 can be downloaded to the client computing device 102 and the server 112 from an external computer via a network (for example, the Internet, a local area network or other, wide area network) and respective network adapters or interfaces 536. From the network adapters or interfaces 536, the software program 108 and the real-time pediatric eye health monitoring and assessment program 110A in the client computing device 102 and the real-time pediatric eye health monitoring and assessment program 110B in the server 112 are loaded into the respective hard drive 530. The network may comprise copper wires, optical fibers, wireless transmission, routers, firewalls, switches, gateway computers and/or edge servers.

Each of the sets of external components 504 a,b can include a computer display monitor 544, a keyboard 542, and a computer mouse 534. External components 504 a,b can also include touch screens, virtual keyboards, touch pads, pointing devices, and other human interface devices. Each of the sets of internal components 502 a,b also includes device drivers 540 to interface to computer display monitor 544, keyboard 542, and computer mouse 534. The device drivers 540, R/W drive or interface 532, and network adapter or interface 536 comprise hardware and software (stored in storage device 530 and/or ROM 524).

It is understood in advance that although this disclosure includes a detailed description on cloud computing, implementation of the teachings recited herein is not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is a service oriented with a focus on statelessness, low coupling, modularity, and semantic interoperability. At the heart of cloud computing is an infrastructure comprising a network of interconnected nodes.

Figure 6:
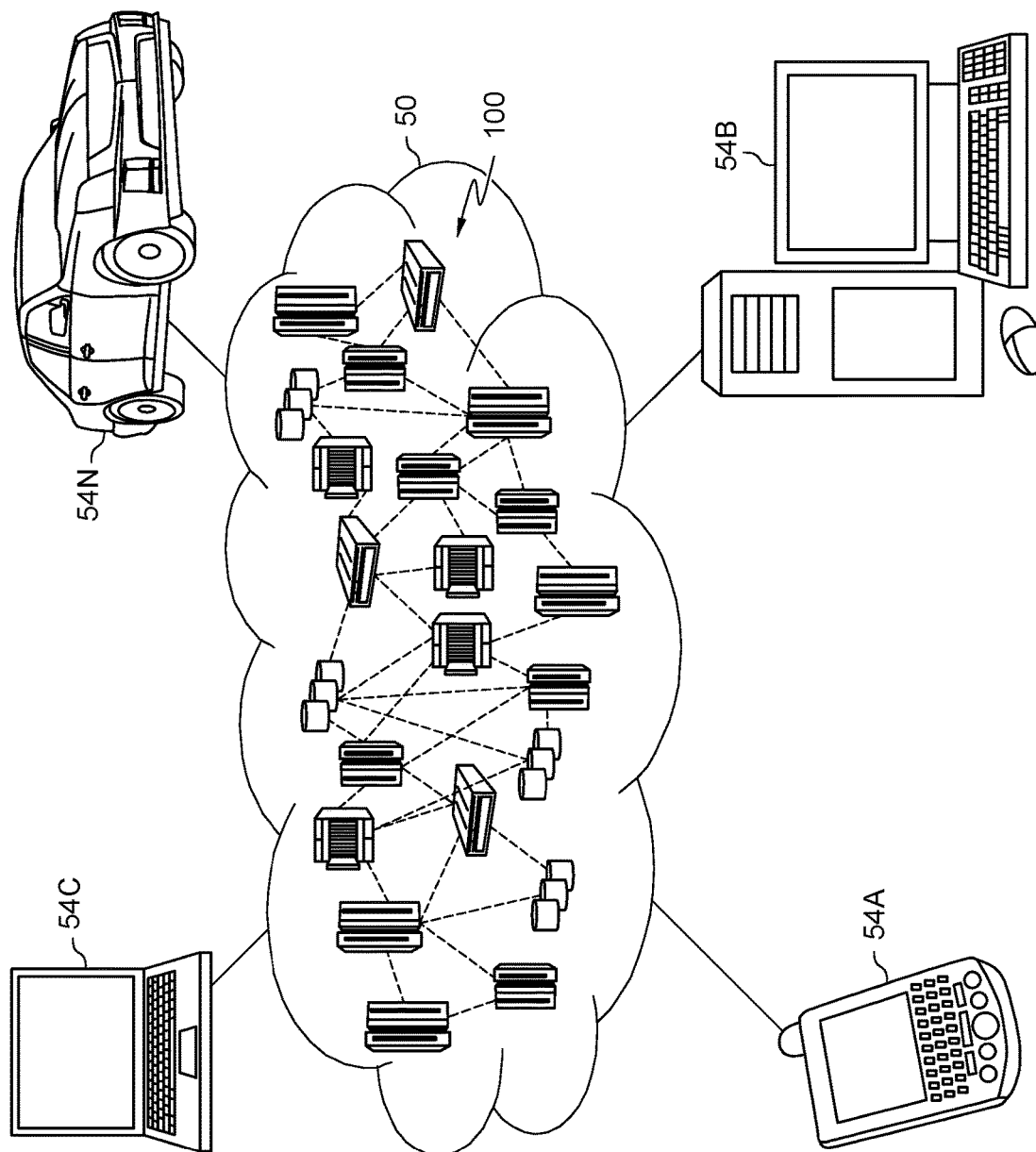
FIG. 6 depicts a cloud computing environment according to an embodiment of the present invention.

Referring now to FIG. 6, illustrative cloud computing environment 50 is depicted. As shown, cloud computing environment 50 comprises one or more cloud computing nodes 100 with which local computing devices used by cloud consumers, such as, for example, personal digital assistant (PDA) or cellular telephone 54A, desktop computer 54B, laptop computer 54C, and/or automobile computer system 54N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 100 and cloud computing environment 50 can communicate with any type of computerized device over any type of network and/or network addressable connection (e.g., using a web browser).

Figure 7:
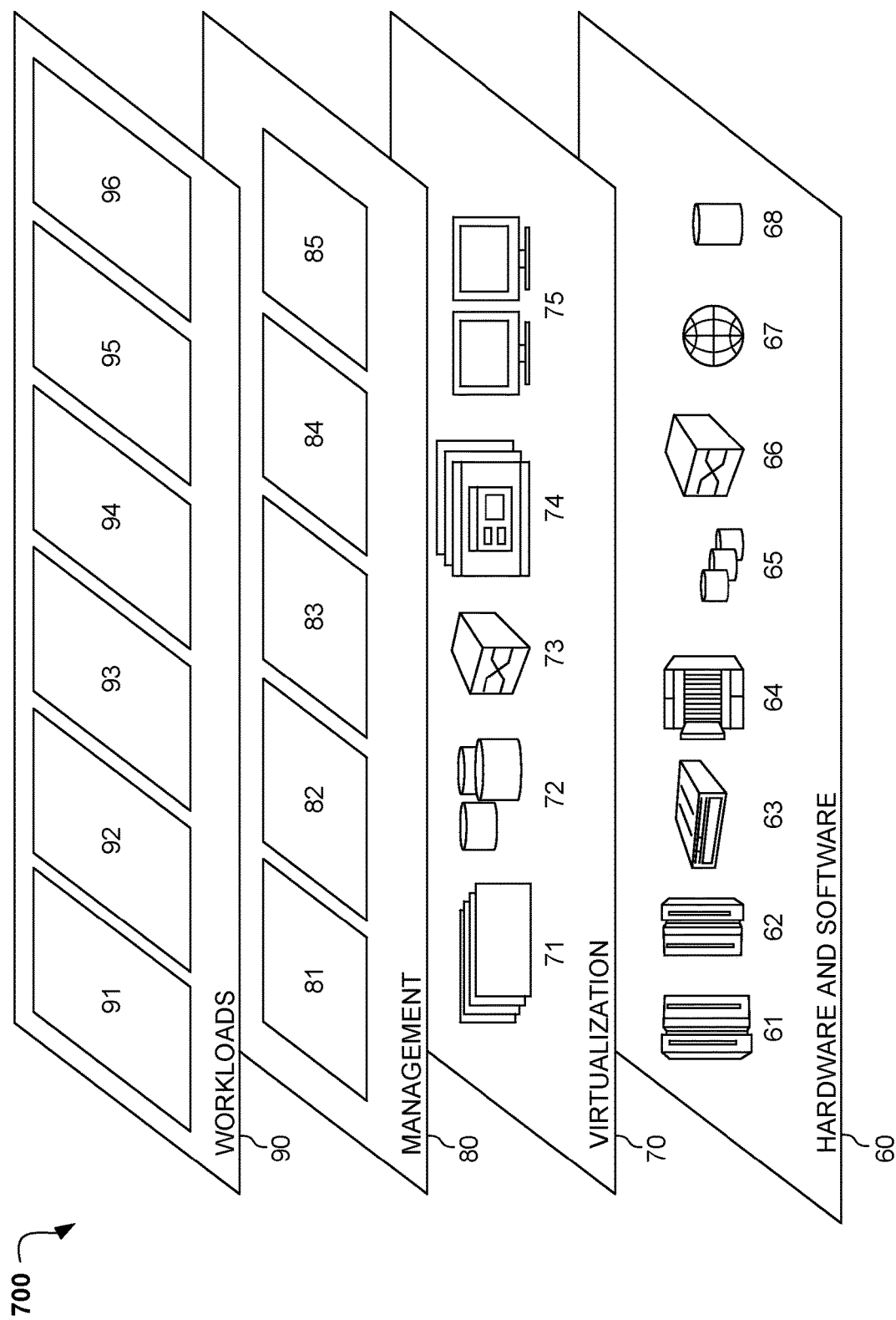
FIG. 7 depicts abstraction model layers according to an embodiment of the present invention.

Referring now to FIG. 7, a set of functional abstraction layers 700 provided by cloud computing environment 50 is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and real-time pediatric eye health monitoring and assessment 96. Real-time pediatric eye health monitoring and assessment 96 may relate to generating a database of clinical alerts and recommendations related to eye health, monitoring various clinical knowledge databases which may provide experts opinions about a particular eye disease.

The descriptions of the various embodiments of the present invention have been presented for purposes of illustration but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A processor-implemented method for real-time pediatric eye health monitoring and assessment, the method comprising:
   receiving, by a processor, a plurality of real-time data related to an individual's eye health from a user device;
   assessing biometric indications relating to eye health based on the plurality of real-time data;
   generating a report on the assessed biometric indications;
   collecting clinical information from one or more databases;
   determining whether the assessed biometric indications reach pre-configured threshold conditions;
   generating alerts and recommendations based on analysis of the collected clinical information and the assessed biometric indications based on the assessed biometric indications satisfying the pre-configured threshold conditions; and
   reconfiguring the display settings of the user device based on the generated alerts and recommendations, wherein the display settings are selected from a group consisting of screen brightness, screen size, and screen resolution.

2. The method of claim 1, wherein the display is automatically turned off when the alerts are critical.

3. The method of claim 1, wherein the plurality of real-time data is selected from a group consisting of a distance of the user's eyes from a display screen, a blink rate of the user, gestures, tear film integrity, and the distance between the user's pupils.

4. The method of claim 1, further comprising:
   collecting data regarding environmental factors including temperature, humidity, lighting conditions and air quality from a home monitoring system.

5. The method of claim 4, further comprising:
   receiving manually-entered data regarding the environmental factors.

6. The method of claim 1, wherein an infra-red sensor is utilized to monitor the distance between a user's pupils and tear film integrity.

7. The method of claim 1, further comprising:
   assessing tear film integrity based on a time taken for tear film to break up, a quadrant of a pupil where a break-up begins, and a ratio of area of a broken tear film to a total area of the pupil.

8. A computer system for real-time pediatric eye health monitoring and assessment, the computer system comprising:
   receiving, by a processor, a plurality of real-time data related to an individual's eye health from a user device;
   assessing biometric indications relating to eye health based on the plurality of real-time data;
   generating a report on the assessed biometric indications;
   collecting clinical information from one or more databases;

determining whether the assessed biometric indications reach pre-configured threshold conditions;

generating alerts and recommendations based on analysis of the collected clinical information and the assessed biometric indications based on the assessed biometric indications satisfying the pre-configured threshold conditions; and reconfiguring the display settings of the user device based on the generated alerts and recommendations, wherein the display settings are selected from a group consisting of screen brightness, screen size, and screen resolution.

9. The computer system of claim 8, wherein the display is automatically turned off when the alerts are critical.

10. The computer system of claim 8, wherein the plurality of real-time data is selected from a group consisting of a distance of the user's eyes from a display screen, a blink rate of the user, gestures, tear film integrity, and the distance between the user's pupils.

11. The computer system of claim 8, further comprising:
collecting data regarding environmental factors including temperature, humidity, lighting conditions and air quality from a home monitoring system.

12. The computer system of claim 11, further comprising:
receiving manually-entered data regarding the environmental factors.

13. The computer system of claim 8, wherein an infra-red sensor is utilized to monitor the distance between a user's pupils and tear film integrity.

14. The computer system of claim 8, further comprising:
assessing tear film integrity based on a time taken for tear film to break up, a quadrant of a pupil where a break-up begins, and a ratio of area of a broken tear film to a total area of the pupil.

15. A computer program product for real-time pediatric eye health monitoring and assessment, the computer program product comprising:
receiving, by a processor, a plurality of real-time data related to an individual's eye health from a user device;

assessing biometric indications relating to eye health based on the plurality of real-time data;

generating a report on the assessed biometric indications;

collecting clinical information from one or more databases;

determining whether the assessed biometric indications reach pre-configured threshold conditions;

generating alerts and recommendations based on analysis of the collected clinical information and the assessed biometric indications based on the assessed biometric indications satisfying the pre-configured threshold conditions; and reconfiguring the display settings of the user device based on the generated alerts and recommendations, wherein the display settings are selected from a group consisting of screen brightness, screen size, and screen resolution.

16. The computer program product of claim 15, wherein the display is automatically turned off when the alerts are critical.

17. The computer program product of claim 15, wherein the plurality of real-time data is selected from a group consisting of a distance of the user's eyes from a display screen, a blink rate of the user, gestures, tear film integrity, and the distance between the user's pupils.

18. The computer program product of claim 15, further comprising:
collecting data regarding environmental factors including temperature, humidity, lighting conditions and air quality from a home monitoring system.

19. The computer program product of claim 15, wherein an infra-red sensor is utilized to monitor the distance between the pupils and the tear film integrity.

20. The computer program product of claim 15, further comprising:
assessing tear film integrity based on a time taken for tear film to break up, a quadrant of a pupil where a break-up begins, and a ratio of area of a broken tear film to a total area of the pupil.

* * * * *